US00PP24273P3

(12) United States Plant Patent
Egger

(10) Patent No.: US PP24,273 P3
(45) Date of Patent: Feb. 25, 2014

(54) ***HEUCHERA* PLANT NAMED 'RIO'**

(50) Latin Name: ***Heuchera* sp.**
Varietal Denomination: Rio

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 139 days.

(21) Appl. No.: 13/506,791

(22) Filed: May 16, 2012

(65) Prior Publication Data

US 2013/0312145 P1 Nov. 21, 2013

(51) Int. Cl.
*A01H 5/00* (2006.01)

(52) U.S. Cl.
USPC ..... Plt./440

(58) Field of Classification Search
USPC ..... Plt./440
See application file for complete search history.

*Primary Examiner* — June Hwu

(74) *Attorney, Agent, or Firm* — Klarquist Sparkman LLP

(57) ABSTRACT

A new and distinct *Heuchera* plant characterized by medium size leaves that change color depending on the temperature, with red spring leaves and veiled summer leaves which change from red to tan, winter leaves are veiled olive green, short flowering stems with showy white flowers, reblooming all spring, summer, fall, an excellent, multi-crowned, medium mounding habit, and excellent vigor.

2 Drawing Sheets

Botanical denomination: *Heuchera* sp.
Variety designation: 'Rio'.

BACKGROUND OF THE INVENTION

The present invention relates to a new and distinct cultivar of *Heuchera* and given the cultivar name of 'Rio'. *Heuchera* is in the family Saxifragaceae. *Heuchera* 'Rio' came out of a planned breeding program to create red leaf *Heuchera*. It had great garden performance in spite of being red in the spring only. This new cultivar originated from a cross between *Heuchera* K201-2, a proprietary non-commercial hybrid, as the seed parent, and *Heuchera* K148-5, a proprietary non-commercial hybrid, as, as the pollen parent.

Compared to the seed parent, *Heuchera* K201-2, the new cultivar has leaves that are larger and more veiled and a bigger habit.

Compared to the pollen parent, *Heuchera* K148-5, the new cultivar is more veiled and has leaves that are a red amber to khaki rather than dark red burgundy.

Compared to *Heuchera* 'Marmalade', U.S. Plant Pat. No. 15,945, the new cultivar has larger leaves that are much less ruffled and less deeply lobed. The new cultivar has showier flowers.

Compared to *Heuchera* 'Autumn Leaves', U.S. Pat. No. 22,103, the new cultivar has greater vigor, a much bigger habit with many more crowns, and doesn't show leaf puckering.

This new *Heuchera* is uniquely distinguished by:

1. medium size leaves that change color depending on the temperature,
2. spring leaves are red; summer leaves are veiled and change from red to tan,
3. winter leaves are veiled olive green,
4. short flowering stems with showy white flowers,
5. reblooming all spring, summer, and fall,
6. excellent, multi-crowned, medium mounding habit,
7. and excellent vigor.

This new cultivar has been reproduced only by asexual propagation (tip cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWINGS

FIG. 2 shows a two-year-old plant of *Heuchera* 'Rio' growing in a one gallon pot in a cold greenhouse in April in Canby, Oreg.

FIG. 3 shows a one-year-old plant of *Heuchera* 'Rio' growing in a one gallon pot in a cold greenhouse in November in Canby, Oreg.

DETAILED PLANT DESCRIPTION

Figure 1:
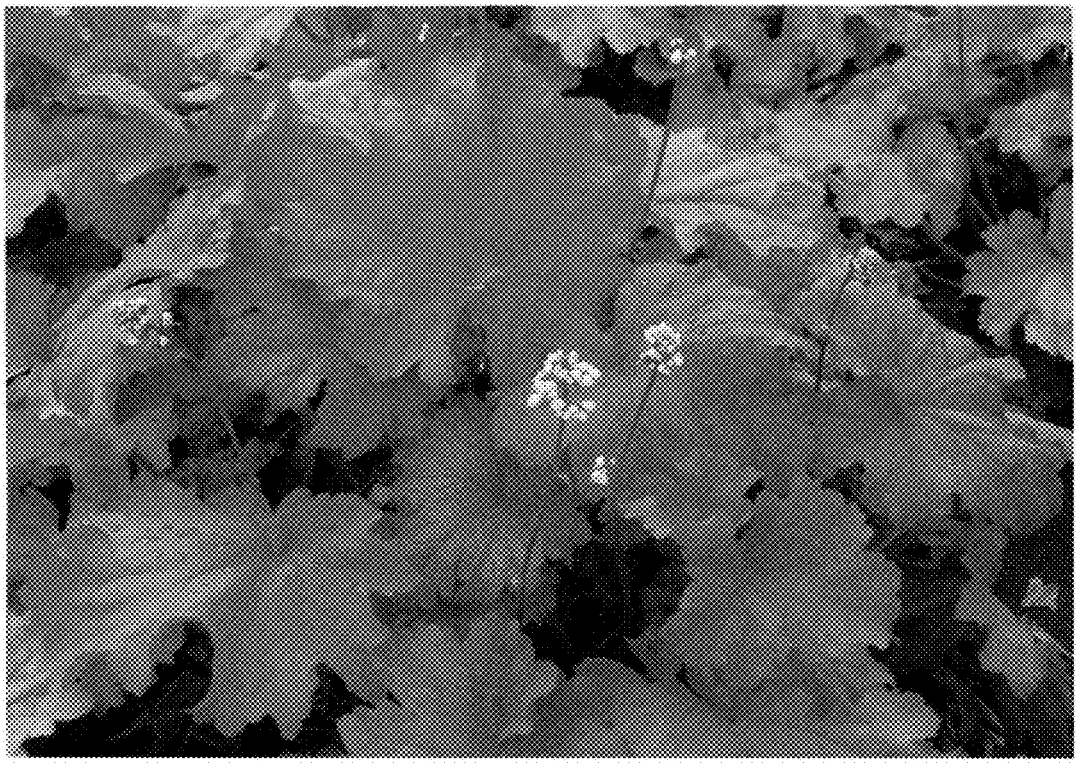
FIG. 1 shows a two-year-old plant of *Heuchera* 'Rio' growing in the trial field in a full sun location in early May in Canby, Oreg.

The following is a detailed description of the new *Heuchera* cultivar based on observations of two-year-old specimens growing in one gallon containers in a cold greenhouse in March in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 2007 edition, $5^{th}$ edition.

Plant:

*Form.*—Basal rosette, herbaceous perennial.

*Hardiness.*—USDA Zone 4 to 9.

*Size.*—25 cm tall from top of the foliage to the ground and 45 cm wide.

*Habit.*—Mounding.

*Vigor.*—Excellent.

Leaf:

*Type.*—Simple.

*Arrangement.*—Rosette.

*Shape.*—Broadly ovate to orbicular.

*Lobing/division.*—5 to 7 lobes, with shallow secondary lobes.

*Venation.*—Palmate.

*Margins.*—Crenate and lightly undulate.

*Apex.*—Mucronulate.

*Base.*—Cordate and overlapping.

*Blade size.*—Grows to 14 cm long and 14 cm wide.

*Surface texture.*—Glandular on top and bottom.

*Petiole description.*—Grows to 19 cm long and 4 mm wide, glandular hairs, Greyed Purple 187C.

*Leaf color.*—Color variable, topside depending on temperature and light conditions, spring leaves Red 46A; summer leaves between Greyed Purple 183B and Brown 200C with the veins Greyed Purple 183C; fall to winter leaves Grey Brown N199A with veil Black 202C; bottom side same for all seasons Greyed Purple 187C.

Inflorescence:

*Size.*—Grows to 4 cm wide and 11 cm long.

*Type.*—Thyrse.

*Number of flowers per thyrse.*—About 70.

*Number of thyrse.*—About 10 in the first spring flush, reblooming all summer.

*Peduncle.*—Grows to 25 cm long, 3 mm wide at base, Greyed Purple 187B, glandular hairs.

*Pedicel.*—Variable in size, with glandular hairs, Greyed Purple 187B.

*Bloom period.*—May through October in Canby, Oreg.

Flower bud:

*Size.*—3 mm wide and 5 mm long.

*Description.*—Glandular puberulent, ovoid, down facing.

*Color.*—White NN155C on the top ⅔ and Red 49C on bottom ⅓.

Flower:

*Type.*—Perfect.

*Shape.*—Campanulate.

*Size.*—6 mm long and 4 mm wide.

*Corolla description.*—5 petals, 3.5 mm long and 0.5 mm wide, narrowly spatulate, margins entire, tip acute, glabrous top and glandular on bottom, White NN155C.

*Calyx description.*—Campanulate, 5 mm long and 4 mm wide, with 5 lobes divided ½ way to the base, each 2 mm wide and 2.5 mm long, glandular hairs outside and glabrous inside, tips obtuse, margin entire; color both sides White NN155B with the bottom ⅓ changing from Red 49D when just open to Yellow 2C when very mature.

*Stamen description.*—5 in number, filaments 3 mm long, White NN155C, anthers 0.2 mm, Greyed Orange 164B, pollen none.

*Pistil description.*—1, 2-beaked, 6 mm long and 2.5 mm wide; White NN155C overall, ovary 2.5 mm long and 2.5 mm wide; style 3.5 mm long.

*Fragrance.*—None.

*Lastingness.*—Each thyrse blooms for about 3 weeks on the plant.

Fruit:

*Type.*—Two-beaked ovoid capsule.

*Fertility.*—Low.

*Color.*—Greyed Brown 199C.

Seed:

*Shape.*—Linear.

*Size.*—2 mm long.

*Color.*—Black 202A.

Pest and disease tolerance: The new cultivar is typical to the genus. No known resistances to pests or diseases. No problems have been found in Canby, Oreg.

I claim:

1. A new and distinct *Heuchera* plant as herein illustrated and described.

* * * * *

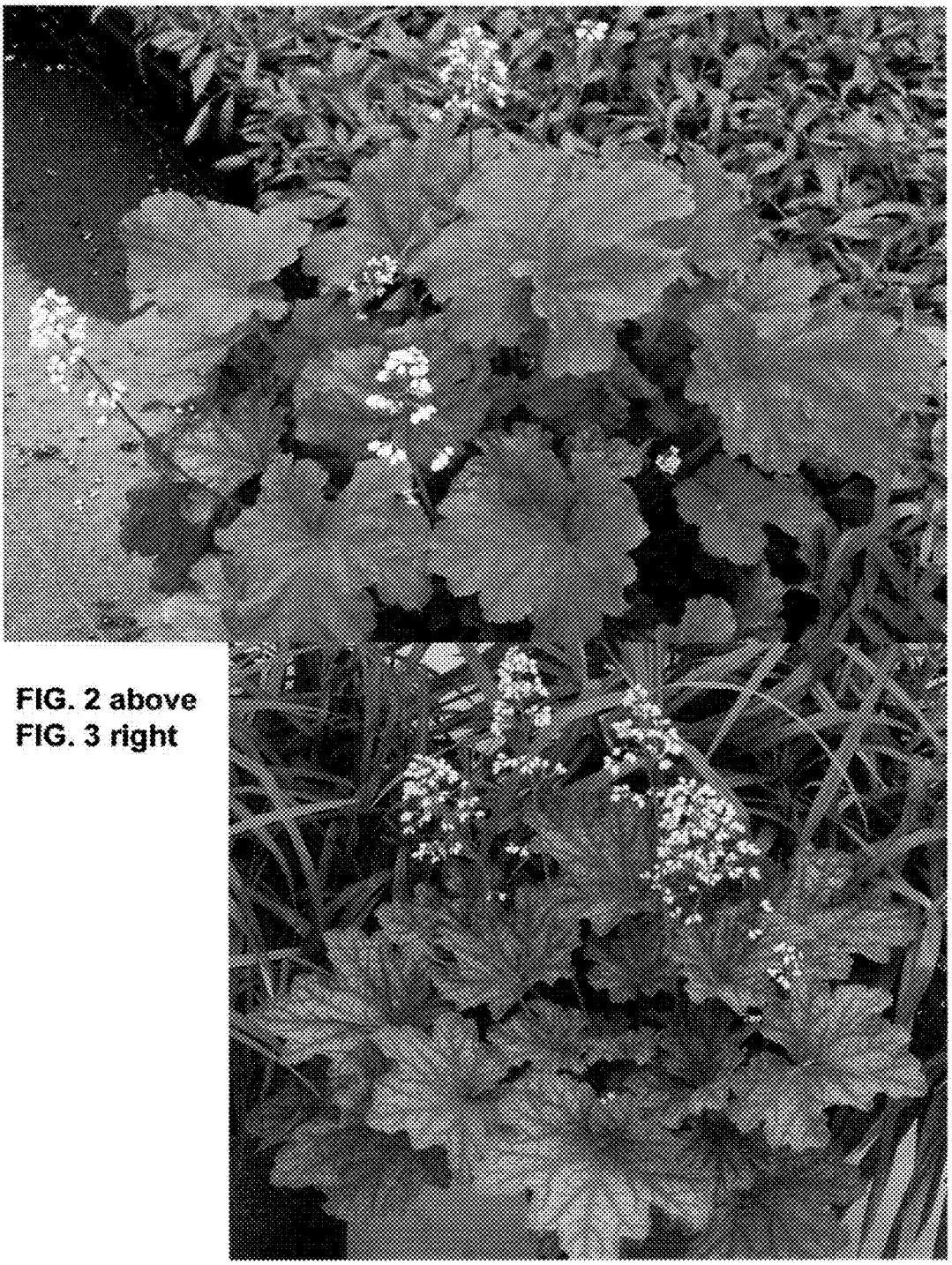
FIG. 2 above
FIG. 3 right